United States Patent [19]

Senyei et al.

[11] Patent Number: 5,079,171

[45] Date of Patent: Jan. 7, 1992

[54] DETERMINING PREGNANCY INDUCED HYPERTENSION AND ECLAMPSIA BY IMMUNOASSAY OF CELLULAR FIBRONECTIN

[75] Inventors: Andrew E. Senyei, Santa Ana; Nelson N. H. Teng, Hillsborough, both of Calif.

[73] Assignee: Adeza Biomedical Corporation, Sunnyvale, Calif.

[21] Appl. No.: 302,854

[22] Filed: Jan. 27, 1989

Related U.S. Application Data

[63] Continuation-in-part of Ser. No. 244,970, Sep. 15, 1988, abandoned.

[51] Int. Cl.$^5$ ............................................. G01N 33/53
[52] U.S. Cl. .................................... 436/510; 436/518; 436/536; 436/65; 436/814
[58] Field of Search ............... 436/510, 518, 536, 538, 436/547, 548, 63, 65, 811, 814

[56] References Cited

U.S. PATENT DOCUMENTS 4,980,279 12/1990 Peters et al.

OTHER PUBLICATIONS

Yamada, K. M., "Fibronectin and Other Structural Proteins", *Cell Biology of the Extracellular Matrix*, Hay, E. D. (ed.), Plenum Press, pp. 95-97 (1981).

Saleh et al., "Hemostasis in Hypertensive Disorders of Pregnancy", *Hemostasis and Hypertension*, vol. 71(5), pp. 719-722 (1988).

Ermolin et al., "Quantitative Immunoenzymic Assay of Fibronectin in Biological Fluids", *Chemical Abstracts*, vol. 106:46781r (1987).

Canavaggio et al., "Measurement of Human Fibronectin by Enzyme Immunoassay Using Monoclonal Antibodies", *Chemical Abstracts*, vol. 100:47905x (1984).

Wisdom, G. B., "Enzyme-Immunoassay", *Clinical Chemistry*, vol. 22(8), pp. 1243-1255 (1976).

Gutman, A. et al., *Proc. Natl. Acad. Sci. U.S.A.* 84:7179-7182 (1987).

*Primary Examiner*—Sam Rosen
*Attorney, Agent, or Firm*—Skjerven, Morrill, MacPherson, Franklin & Friel

[57] ABSTRACT

Preeclampisa, pregnancy induced hypertension (PIH) and eclampsia are determined by identifying the presence of an endothelial cell marker in a sample of blood, plasma or serum of a pregnant woman using a sandwich or competition immunoassay. Cellular fibronectin marker in a sample is determined by binding with an anti-(cellular fibronectin) antibody. Reagents for these methods are also an aspect of the invention.

14 Claims, No Drawings

DETERMINING PREGNANCY INDUCED HYPERTENSION AND ECLAMPSIA BY IMMUNOASSAY OF CELLULAR FIBRONECTIN

RELATIONSHIP TO COPENDING APPLICATIONS

This application is a continuation-in-part of copending, commonly assigned U.S. patent application Ser. No. 07/244,970 filed Sept. 15, 1988, now abandoned.

FIELD OF THE INVENTION

This invention relates to methods, reagents and kits for detection of pregnancy induced hypertension (PIH) or preeclampsia during pregnancy. In particular, this invention is directed to the determination of PIH or preeclampsia by testing whole blood, serum or plasma samples for the presence of a marker for endothelial cell injury, for example cellular fibronectin.

BACKGROUND OF THE INVENTION

Preeclampsia, eclampsia and pregnancy induced hypertension (PIH) are characterized by elevated blood pressure, proteinuria, and edema. The cause and nature of these disorders is only partially understood. Preeclampsia and PIH are often used to designate the same disorders. The term "preeclampsia" is used hereinafter, for purposes of clarity of explanation, not by way of limitation, to broadly include preeclampsia, pregnancy induced hypertension, and eclampsia. Although considered to be relatively rare in the United States, preeclampsia occurs worldwide in from 2 to 35 percent of pregnancies, depending on diagnostic criteria and study population. Deaths from preeclampsia are nearly equal to those from eclampsia in a recent report by Redman, C. Brit.Med.J. 296:1209-1210 (April, 1988). However, tests for these conditions are often ambiguous, and diagnosis of these conditions have often not been possible until the condition had progressed. A reliable test for early diagnosis of this condition is critically needed.

A review of the role of prostaglandins in preeclampsia was published by Friedman, S. Obstet.Gynecol. 71:1-22-137 (1988). Examination of maternal fluids for metabolic markers for PIH and preeclampsia has revealed that urine levels of 2,3-dinor-6-keto PG $F_{1\alpha}$ increase during this condition, Ob/Gyn Topics, 2:5 (1987). Levels of other substances in the blood have also been studied.

A number of studies have focused on the general increase in fibronectin levels in blood during these disease processes: Graninger, W. et al, Europ.J.Obstet.-Gynec.Reprod.Biol., 19:223-229 (1985); Hess, L, et al Obstret.Gynecol. 68:25-28 (1986); Lazarchick, J. et al, Am.J.Ob.Gyn. 154:1050-1052 (1986); Ericksen, H. et al, Acta.Obstet.Gynecol.Scand. 66:25-28 (1987); and Saleh, A. et al, Obstet.Gynecol. 71:719 (1988), for example. Although fibronectin levels in the blood were reportedly higher with PIH and preeclampsia, the degree of increase varied with each individual and stage of pregnancy, and considered alone, was not a reliable diagnostic indicator of the disease. Sibai, B. et al, Contemp.Ob/-Gyn. 57 (Feb. 1988) reports that the search continues for a reliable means for forecasting PIH and effective ways to reduce incidence. In the meantime, clinicians still continue using blood pressure criteria to guide management.

That the elevated fibronectin level observed with preeclampsia suggested endothelial injury was postulated by Bhatia, R. et al, Am.J.Obstet.Gynecol. 157:106-108 (1987). More recently, Roberts (Ob.Gyn.-News. 221 (Nov. 1987) has suggested that the evidence suggests that preeclampsia is a disease process fundamentally related to endothelial cell injury, not a hypertensive disorder.

Monoclonal antibodies which bind preferentially with human cellular fibronectin and can distinguish between the cellular fibronectin and plasma fibronectin are described by Keen, J. et al, Mol.Biol.Med. 2:15-27 (1984). Monoclonal antibodies which bind with a unique Ed sequence of cellular fibronectin in embryonic and adult human tissues are described by Vartio, T. et al, J.CellSci. 88:419-430 (1987). Unique amino acid stretches present in human fibronectin are reported by Gutman, A. et al, Proc.Na;tl.Acad.Sci.USA. 84:7179-7182 (1987). Peters, J. et al, Am.Rev.Respir.Dis. 138:167-174 (1988) describes the synthesis of an Extra Type III Domain (ED1) peptide corresponding to a unique nonhomologous stretch of 29 amino acids present in human cellular fibronectin, antibodies binding with this region, and an ELISA immunoassay developed with these antibodies. The peptide sequence disclosed is TYSSPEDGIHELFPAPDGEEDTA-ELQGGC, using the single letter abbreviations for alanine (A), cysteine (C), aspartic acid (D), glutamic acid (E), phenylalanine (F), glycine (G), histidine (H), isoleucine (I), leucine (L), proline (P), glutamine (Q), serine (S), threonine (T), and tyrosine (Y).

SUMMARY OF THE INVENTION

Preeclampisa, pregnancy induced hypertension (PIH) and eclampsia are determined by identifying the presence of an endothelial cell marker in a sample of blood, plasma or serum of a pregnant woman using a sandwich or competition immunoassay.

In one embodiment, the presence of the endothelial cell marker in the sample is determined by contracting the sample with an anti-(endothelial cell marker) antibody, and determining the binding of the antibody with the endothelial cell marker. The sample can be contacted with an insoluble support to which a first anti-(endothelial cell marker) antibody is adhered for a time sufficient to permit antigen-antibody binding to occur; the insoluble support can then be contacted with a second anti-(endothelial cell marker) antibody for a time sufficient to permit antigen-antibody binding to occur; and the presence of second anti-(endothelial cell marker) antibody on the insoluble support can be determined. The second anti-(endothelial cell marker) antibody can have a physically detectable label. Alternatively, the method can comprise contacting a mixture of the sample and a second anti-(endothelial cell marker) antibody with an insoluble support to which a first anti-(endothelial cell marker) antibody is adhered for a time sufficient to permit antigen-antibody binding to occur; and determining the presence of second anti-(endothelial cell marker) antibody on the insoluble support. The endothelial marker can be cellular fibronectin and the anti-(endothelial cell marker) antibody can be an anti-(cellular fibronectin) antibody. When two different anti-(endothelial marker) antibodies are used and one is an anti-(cellular fibronectin) antibody, the second antibody can be a non-(cross-reacting) antibody or an anti-(fibronectin) antibody.

One competition method of this invention comprises contacting an insoluble support to which an anti-(endothelial cell marker) antibody is adhered with a mixture of the sample and an amount of a labeled endothelial cell marker which is insufficient to bind with all of the anti-(endothelial cell marker) antibody adhered to the support; and determining the amount of labeled endothelial cell marker bound to the insoluble support or the amount of labeled endothelial cell marker remaining in the mixture. In an alternate competition embodiment, the method comprises contacting an insoluble support to which an endothelial cell marker is adhered with a mixture of the sample and an amount of a labeled anti-(endothelial cell marker) antibody which is insufficient to bind with all of the endothelial cell marker adhered to the support; and determining the amount of labeled anti-(endothelial cell marker) antibody bound to the insoluble support or the amount of labeled anti-(endothelial cell marker) antibody remaining in the mixture.

Reagents of this invention comprise anti-(endothelial cell marker) antibody adhered to an insoluble reagent support and endothelial cell marker adhered to an insoluble reagent support.

One testing kit of this invention comprises an anti-(endothelial cell marker) antibody such as anti-(cellular fibronectin) antibody adhered to an insoluble support and labeled anti-(endothelial cell marker) antibody such as labeled anti-(cellular fibronectin) antibody. Another kit comprises an anti-(fibronectin) antibody adhered to an insoluble support and labeled anti-(cellular fibronectin) antibody. A still further kit comprises an anti-(endothelial cell marker) antibody adhered to an insoluble support and labeled endothelial cell marker. Another kit comprises an endothelial cell marker adhered to an insoluble support and labeled anti-(endothelial cell marker) antibody.

The reagents can be present in any suitable form in the kit, for example in separate containers, packages, and the like.

DETAILED DESCRIPTION OF THE INVENTION

The object of this invention is the detection of preeclampisa, pregnancy induced hypertension (PIH) and eclampsia by identifying the presence of an endothelial cell marker in a sample of blood, plasma or serum of a pregnant woman using a sandwich or competition immunoassay.

The term "endothelial cell marker", as used herein, is defined to mean a chemical or substance which is present in the blood of a pregnant woman when she has a process or condition of preeclampsia, PIH or eclampsia and which is not present in significant amounts during normal pregnancy. The term "anti-(endothelial cell marker) antibody", as used herein, is defined to mean an antibody (affinity purified polyclonal or monoclonal) which preferentially binds with an endothelial cell marker and not significantly with blood components present in normal pregnancy.

One endothelial cell marker is endothelial cell fibronectin, hereinafter referred to as cellular fibronectin. Cellular fibronectin derives from endothelial cells which are ruptured or disturbed in the disease process of preeclampsia, PIH or eclampsia It is distinguished from plasma fibronectin which is of hepatic origin or from fetal fibronectin, which originates from fetal cells. Fetal fibronectin is not present in significant amounts in maternal blood during pregnancy. The term "anti-(cellular fibronectin) antibody", as used herein, is defined to include antibodies (affinity purified polyclonal or monoclonal) which preferentially bind with endothelial cell fibronectin and do not bind significantly with plasma fibronectin.

The term "anti-(fibronectin) antibody", as used herein, is defined to include antibodies which bind with total fibronectin components of blood, including plasma fibronectin and endothelial cell fibronectin, or only with cellular fibronectin.

The term "antibody" as used herein is defined to include antibodies of classes IgG, IgM, IgA, IgD, and IgE, and binding fragments, half-antibodies, and hybrid derivatives of antibodies including, but not limited to Fab, and F(ab')$_2$ fragments of antibodies.

The term "preferentially bind" and "preferentially binding", as used herein, is defined to include antibodies and fragments thereof which have less than 10 percent and preferably less than 5 percent cross-reactivity.

In the method of this invention, a blood sample is collected from the patient by conventional procedures. It can be collected from a capillary or vein. It can be drawn into an evacuated container and mixed with heparin, sodium citrate or EDTA and centrifuged to remove cells, yielding plasma. It can be clotted, and serum separated from the clot. It can be absorbed by an absorbent material such as paper and dried.

The detection of the endothelial cell marker can be determined by any suitable procedure. Immunological methods are most convenient for carrying out this method because of their specificity, and the term "immunoassays" as used herein is defined to mean methods using a preferential binding property of an endothelial cell marker with a second material, a binding partner, usually an antibody or another substance having an antigen binding site which binds selectively and preferably preferentially with an epitope of the endothelial cell marker. Included within the scope of this invention are all immunoassay methods including this step, including but not limited to sandwich, competition, agglomeration, precipitation, transistor bridge probe, particle sorting, light disturbing, light scattering, and ultrasonic probe immunoassays, for example. Appropriate immunoassays may use, as labels, radioisotopes, enzymes, or fluorogenic, chromogenic, or chemiluminescent substances.

In one preferred embodiment of this invention, the sample is contacted with an insoluble support to which anti-(endothelial cell marker) antibody is adhered to effect binding and capture of endothelial cell marker in the sample. The insoluble support is then contacted with an unlabeled or labeled antibody which binds with the endothelial cell marker adhering to the insoluble support to detect and measure the captured endothelial cell marker. For example, anti-(endothelial cell marker) antibody can be adhered to the insoluble support, and labeled or unlabeled anti-(endothelial cell marker) antibody can be used to detect the captured antigen.

A preferred endothelial cell marker in the method and reagents of this invention is cellular fibronectin, and the description of the invention hereinafter will be often be in reference to the detection of cellular fibronectin in a sample, for purposes of clarity and not by way of limitation; the invention is intended to include the detection of any endothelial cell marker in patient blood, serum or plasma.

One method for determining preeclampsia, pregnancy induced hypertension or eclampsia comprises obtaining a blood, plasma or serum sample from a pregnant patient; and determining the presence of a endothelial cell marker in the sample. The presence of the endothelial cell marker in the sample can be determined by contracting the sample with an anti-(endothelial cell marker) antibody, and determining the binding of the antibody with the endothelial cell marker. This can be accomplished by the steps of contacting the sample with an insoluble support to which a first anti-(endothelial cell marker) antibody is adhered for a time sufficient to permit antigen-antibody binding to occur; contacting the insoluble support with a second anti-(endothelial cell marker) antibody for a time sufficient to permit antigen-antibody binding to occur; and determining the presence of second anti-(endothelial cell marker) antibody on the insoluble support. The second anti-(endothelial cell marker) antibody can have a physically detectable label. Alternatively, this can be accomplished by contacting a mixture of the sample and a second anti-(endothelial cell marker) antibody with an insoluble support to which a first anti-(endothelial cell marker) antibody is adhered for a time sufficient to permit antigen-antibody binding to occur; and determining the presence of second anti-(endothelial cell marker) antibody on the insoluble support.

In preferred embodiments of this invention, the endothelial cell marker is cellular fibronectin. In this instance, the method can comprise the steps of contacting sample with an anti-(cellular fibronectin) antibody for a time sufficient to permit antigen-antibody binding with the anti-(cellular fibronectin) antibody to occur; and determining the presence of said binding. The method can comprise the steps of contacting the sample with an insoluble support to which anti-(cellular fibronectin) antibody is adhered for a time sufficient to permit antigen-antibody binding to occur; contacting the insoluble support with an anti-(fibronectin) antibody for a time sufficient to permit antigen-antibody binding to occur; and determining the presence of anti-(fibronectin) antibody on the insoluble support. The anti-(fibronectin) antibody can have a physically detectable label. The anti-(fibronectin) antibody can be an anti-(cellular fibronectin) antibody. In one embodiment, the anti-(cellular fibronectin) antibody adhered to the insoluble support is a first anti-(cellular fibronectin) antibody, and the anti-(fibronectin) antibody is a second anti-(cellular fibronectin) antibody which does not significantly cross-react with the first anti-(cellular fibronectin) antibody.

In an alternate method, the steps comprise contacting a mixture of the sample and an anti-(fibronectin) antibody with an insoluble support to which an anti-(cellular fibronectin) antibody is adhered for a time sufficient to permit antigen-antibody binding to occur; and determining the presence of anti-(fibronectin) antibody on the insoluble support. The anti-(fibronectin) antibody can have a physically detectable label, the anti-(cellular fibronectin) antibody can be a first anti-(cellular fibronectin) antibody, and the anti-(fibronectin) antibody can be a second anti-(cellular fibronectin) antibody which does not significantly cross-react.

Another method comprises the steps of contacting the sample with an insoluble support to which anti-(fibronectin) antibody is adhered for a time sufficient to permit antigen-antibody binding to occur; contacting the insoluble support with an anti-(cellular fibronectin) antibody for a time sufficient to permit antigen-antibody binding to occur; and determining the presence of anti-(cellular fibronectin) antibody on the insoluble support. The anti-(cellular fibronectin) antibody can have a physically detectable label. Alternatively, the steps cam comprise contacting a mixture of the sample and an anti-(cellular fibronectin) antibody with an insoluble support to which an anti-(fibronectin) antibody is adhered for a time sufficient to permit antigen-antibody binding to occur; and determining the presence of anti-(cellular fibronectin) antibody on the insoluble support. In this alternate embodiment the anti-(cellular fibronectin) antibody can have a physically detectable label.

One competition immunoassay embodiment of this invention comprises contacting an insoluble support to which an anti-(endothelial cell marker) antibody is adhered with a mixture of the sample and an amount of a labeled endothelial cell marker which is insufficient to bind with all of the anti-(endothelial cell marker) antibody adhered to the support; and determining the amount of labeled endothelial cell marker bound to the insoluble support or the amount of labeled endothelial cell marker remaining in the mixture. The preferred embodiment of this method comprises contacting an insoluble support to which an anti-(cellular fibronectin) antibody is adhered with a mixture of the sample and an amount of a labeled cellular fibronectin which is insufficient to bind with all of the anti-(cellular fibronectin) antibody adhered to the support; and determining the amount of labeled cellular fibronectin bound to the insoluble support or the amount of labeled cellular fibronectin remaining in the mixture.

An alternative competition immunoassay of this invention comprises contacting an insoluble support to which an endothelial cell marker is adhered with a mixture of the sample and an amount of a labeled anti-(endothelial cell marker) antibody which is insufficient to bind with all of the endothelial cell marker adhered to the support; and determining the amount of labeled anti-(endothelial cell marker) antibody bound to the insoluble support or the amount of labeled anti-(endothelial cell marker) antibody remaining in the mixture. A preferred embodiment of this invention comprises contacting an insoluble support to which cellular fibronectin is adhered with a mixture of the sample and an amount of a labeled anti-(cellular fibronectin) antibody which is insufficient to bind with all of the cellular fibronectin adhered to the support: and determining the amount of labeled anti-(cellular fibronectin) antibody bound to the insoluble support or the amount of labeled anti-(cellular fibronectin) antibody remaining in the mixture.

The anti-(endothelial cell marker) antibody can be obtained from the endothelial cell marker, for example, cellular fibronectin, preferably from highly purified cellular fibronectin, by conventional antiserum (polyclonal) or monoclonal techniques. Anti-(plasma fibronectin) antibody can be derived from plasma fibronectin by conventional antiserum (polyclonal) techniques or by monoclonal antibody techniques.

Suitable monoclonal antibodies which bind preferentially with human cellular fibronectin and can distinguish between the cellular fibronectin and plasma fibronectin are described by Keen, J. et al, *Mol.Biol.Med.* 2:15-27 (1984). Monoclonal antibodies which bind with a unique Ed sequence of cellular fibronectin in embryonic and adult human tissues are described by Vartio, T. et al, *J.Cell.Sci.* 88:419-430 (1987). Unique amino acid stretches which can be used to prepare polyclonal and monoclonal antibodies which bind preferentially with human cellular fibronectin are reported by Gutman, A. et al, *Proc.Na;tl.Acad.Sci.USA.* 84:7179-7182 (1987). Peters, J. et al, *Am.Rev.Respir.Dis.* 138:167-174 (1988) describes the synthesis of an Extra Type III Domain (ED1) peptide corresponding to a unique nonhomologous stretch of 29 amino acids present in human cellular fibronectin, antibodies binding with this region, and an ELISA immunoassay developed with these antibodies. The peptide sequence disclosed is TYSSPEDGIHELF-PAPDGEEDTAELQGGC, using the single letter abbreviations for alanine (A), cysteine (C), aspartic acid (D), glutamic acid (E), phenylalanine (F), glycine (G), histidine (H), isoleucine (I), leucine (L), proline (P), glutamine (Q), serine (S), threonine (T), and tyrosine (Y). Each of the antibodies reported by these publications can be used as the anti-(endothelial cell marker) in the method of this invention, and the entire contents of each of the above-described publications and each of the publications cited therein are hereby incorporated by reference.

Polyclonal anti-(cellular fibronectin) antibody can be obtained by immunizing an animal such as a rabbit, guinea pig, rat or goat with concentrated cellular fibronectin, removing serum from the immunized animal, and separating the immunoglobulins from the serum, for example by ammonium sulfate precipitation. The principal antibodies useful in the method of this invention are IgG and IgM antibodies, although the IgD, IgE and IgA antibodies can also be used if available in sufficient quantity. The cellular fibronectin antibodies are then affinity purified using conventional affinity chromatography techniques such as those described by Mishell and Shilgi in SELECTED METHODS IN CELLULAR IMMUNOLOGY. San Francisco: Freeman (1980), Goding, J., MONOCLONAL ANTIBODIES: PRINCIPLES AND PRACTICE. New York: Academic Press pp 111-114 (1983), and Parikh, I., et al, C&EN (Aug. 26, 1985), the entire contents of each of which are hereby incorporated by reference. Suitable absorbency for use in affinity chromatography include cross-linked agarose and cross-linked polyacrylamides to which the cellular fibronectin antibody is covalently bound. For removal of antibodies cross-reacting with plasma fibronectins, the antibody serum is passed through columns to which are coupled plasma fibronectins. A portion of the eluant containing the remaining antibody can then be passed through a cellular fibronectin column and eluted to yield the affinity purified antibody.

In these procedures, the antibody solution can be applied to the column in a phosphate buffered saline solution, and the antibodies can be eluted with a 2.5M NaSCN solution, pH 8.0. Antibody concentration, if desired, can be achieved by negative pressure dialysis or ultrafiltration. Repetition of this procedure may be required to achieve the desired purity. Repetition of the column separation procedures is continued until the desired separation and purity is achieved.

Monoclonal anti-(cellular fibronectin) antibody can be obtained by the methods of Glafre and Milstein, *Methods of Enzym.* 73:1 (1981), immunizing mice with cellular fibronectin to obtain the spleen cells for hybridization. Suitable procedures are described by Goding, J. (supra, pp 56-97), the entire contents of which are hereby incorporated by reference. For production of cellular fibronectin which also binds to fetal fibronectin, the procedures described by Matsuura, H. and Hakomori, S. (supra) can be followed, replacing the tumor fibronectin with fetal fibronectin. Suitable procedures for preparing these antibodies are described in copending, commonly assigned application Ser. No. 121,.895 filed Nov. 17, 1987 and hereby incorporated by reference in its entirety.

Anti-(fibronectin) antibodies of both polyclonal and monoclonal varieties are generally well known and available either commercially or from publicly available hybridoma deposits. For example, anti-(total fibronectin) monoclonal antibodies can be derived from clone samples from ATCC HB 91 (American Type Culture Collection, Rockville, Md.). Such antibodies are also described in Japanese Patent Application 60091264 (DIALOG database file 351, WPI Acc. No. 85-161617/27).

The preferentially binding antibody fragments suitable for use in the device, kit and method of this invention can be made from the respective monoclonal or polyclonal antibodies by conventional enzyme or chemical fragmentation procedures. Suitable procedures are described by Tijssen, P. LABORATORY TECHNIQUES IN BIOCHEMISTRY AND MOLECULAR BIOLOGY: PRACTICE AND THEORIES OF ENZYME IMMUNOASSAYS. New York: Elsevier (1985), for example.

The antibody reagents can be bonded to an insoluble support by conventional processes. Procedures for binding of antibodies to insoluble supports are described in U.S. Pat. Nos. 3,551,555, 3,553,310, 4,048,298 and RE-29,474, and by Tijssen (supra pp 297-328), for example. Procedures for binding of antibodies to polystyrene by adsorption are described in U.S. Pat. Nos. 3,646,346 and 4,092,408, for example.

A variety of materials can be used as the insoluble support, the primary consideration being the binding of the anti-(cellular fibronectin) antibody or the anti-(fibronectin) antibody to the surface, the absence of interference with the reagent binding reaction or with other reactions which can be employed to determine the presence and extent of the binding reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble support are the latexes of the above polymers, silica gel, silicon wafers, glass, paper, insoluble protein, metals, metalloids, metal oxides, magnetic materials, semi-conductive materials, cermets and the like. In addition are included substances which form gels, e.g. proteins such as gelatins, lipopolysaccharides, silicates, agarose, polyacrylamides or polymers which form several aqueous phases such as dextrans, polyalkylene glycols (alkyene with 2 to 3 carbon atoms) or surfactants, e.g. amphophilic compounds such as phospholipids, long chain (12-24 carbon atoms) alkyl ammonium salts, and the like.

The preferred support comprises a nylon or nitrocellulose membrane. An alternate diagnostic support is made from polystyrene, styrene copolymers such as styrene-acrylonitrile copolymers, or polyolefins such as polyethylene or polypropylene, and acrylate and methacrylate polymers and copolymers. The anti-(cellular fibronectin) reagent antibody, other antibody reagents, and cellular fibronectin reagent can be bound to the insoluble support by adsorption, ionic bonding, van der Waals adsorption, electrostatic bonding, or other non-covalent bonding, or it can be bound to the insoluble support by covalent bonding. A particularly advantageous support for this procedure comprises a microtiter plate having a plurality of wells. The well surface or plastic cup inserts therein can constitute the antigen or antibody support. If the determination will require the use of fluorometric measurements, the microtiter plate or the well inserts are advantageously opaque to light so that excitation light applied to a well does not reach or influence contents of the surrounding wells.

Procedures for non-covalent bonding are described in U.S. Pat. No. 4,528,267. Procedures for covalently bonding antibodies and antigens to insoluble supports are described by Ichiro Chibata in IMMOBILIZED ENZYMES. Halsted Press: New York (1978) and A. Cuatrecasas, *J.Bio.Chem.* 245:3059 (1970), the entire contents of which are hereby incorporated by reference. The surface can be coated with a protein and coupled with the antibody or antigen using procedures described in U.S. Pat. No. 4,210,418 using glutaraldehyde as a coupling agent, for example. In a still further procedure, the well can be coated with a layer having free isocyanate groups such as a polyether isocyanate, and application of the antibody or antigen in aqueous solution thereto effects the requisite bonding. In a still further procedure, the antibody or antigen can be coupled to a hydroxylated material by means of cyanogen bromide as described in U.S. Pat. No. 3,720,760.

The insoluble supports are preferably "blocked" to reduce non-specific binding. The choice of suitable blocking agents in determined by the type of insoluble support. For example, for polystyrene supports, suitable blocking agents include water-soluble non-immune animal proteins. Suitable water-soluble non-immune animal proteins include bovine (BSA), human, rabbit, goat, sheep, and horse serum albumins; casein and non-fat milk; ovalbumin, glycoproteins, and the like.

The same blocking agents can also be used for nylon and nitrocellulose supports. However, a preferred blocking agent for nitrocellulose or nylon membrane supports is non-fat milk or casein. An optimum blocking agent for these membrane supports is an aqueous solution containing from 1 to 5 wt. % non-fat dried milk or casein, and nonionic surfactants such as polyoxyethylene sorbitan derivatives and polyoxyethylene ethers.

The labeled anti-(cellular fibronectin) antibody, anti-(fibronectin) antibody and anti-(antibody) reagents of this invention can be prepared by conventional procedures for attaching labels to proteins, preferably with suitable protection of antibody binding sites. The labels can be bonded or coupled to the protein reagents by chemical or physical bonding. Ligands and groups which can be bound to the antibodies of this invention include elements, compounds or biological materials which have physical or chemical characteristics which can be used to distinguish the reagents to which they are bonded from compounds and materials in the sample being tested.

Radiolabeled anti-(fibronectin or cellular fibronectin antigen) antibodies of this invention can be used for in vitro diagnostic tests. The specific activity of a tagged antibody depends upon the half-life, isotopic purity of the radioactive label and how the label is incorporated into the antigen or antibody. Table A lists several commonly used isotopes, their specific activities and half-lives. In immunoassay tests, the higher the specific activity, in general, the better the sensitivity.

TABLE A

| Isotope | Specific Activity of Pure Isotope (Curies/mole) | Half-Life |
|---------|------------------------------------------------|-----------|
| $^{14}C$ | $6.25 \times 10^1$ | 5720 years |
| $^3H$ | $2.91 \times 10^4$ | 12.5 years |
| $^{35}S$ | $1.50 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies with radioactive isotopes listed in Table A are generally known in the art. Tritium labeling procedures are described in U.S. Pat. No. 4,302,438, for example. Iodinating, tritium labeling and $^{35}S$ labeling procedures especially adapted for antibodies are described by Goding (supra, pp 124–126), and the references cited therein. Other procedures for iodinating antibodies are described by Hunter and Greenwood, *Nature.* 144:945 (1962), by David et al, *Biochemistry.* 3:1014–1021 (1974), and in U.S. Pat. Nos. 3,867,517 and 4,376,110. Examples of suitable systems, coupling procedures and substrate reactions therewith are disclosed in U.S. Pat. Nos. Re. 31,006, B1 3,654,090, 4,214,048, 4,289,747, 4,302,438, 4,312,943, 4,376,110 and the references cited therein, for example. Examples of other suitable systems are described by Pesce et al, *Clin.Chem.* 20:353–359 (1974) and Wisdom, G., *Clin.-Chem.* 22:1243 (1976).

A list of suitable enzyme classes which can be used for labeling, and specific examples for each class, follow:

TABLE B

| Class | Enzyme Example |
|-------|----------------|
| Hydrolases | Amylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Desmolases | Aldolase |
| Oxidases | Glucose oxidase |
|  | Horseradish peroxidase |
| Phosphatases | Alkaline Phosphatases |
|  | Acid Phosphatases |
| Dehydrogenases | G6PDH (Glucose 6-6-phosphodehydrogenase) |
| β-galactosidase |  |
| Phosphorylases |  |
| Hexokinases |  |

A list of suitable enzymes are described in Hawk, et al. PRACTICAL PHYSIOLOGICAL CHEMISTRY, New York: McGraw-Hill pp 306–397 (1954).

Fluorogenic and chromogenic enzymes (enzymes in the presence of which a selected substrate will produce a fluorescent or chromogenic product) are useful labeling moieties. Methods for selectively conjugating enzymes to antibodies without impairing the ability of the antibody to bind with antigen and for conjugating enzymes to proteinaceous reagents are well known in the art.

Suitable enzymes and procedures for coupling them to antibodies are described by Ichiro Chibata in IMMOBILIZED ENZYMES (supra); A. Cuatrecasas, *J.Bio.-Chem.* (supra); Wilson, M. et al, *INTERNATIONAL CONFERENCE IN IMMUNOFLUORESCENCE AND RELATED STAINING TECHNIQUES.* W. Knapp et al, editors. Amsterdam: Elsevier pp 215-244 (1978); Sullivan, M. et al, *Annals of Clinical Biochemistry.* 16:221-240 (1979); Nygren, H. et al, *Medical Biology.* 57:187-191 (1979); Gadkari, D. et al, *Journal of Virological Methods.* 10:215-224 (1985); Tijssen, P. et al, *Analytical Biochemistry.* 136:451-457 (1984); Tsuruta, J. et al, *The Journal of Histochemistry and Cytochemistry.* 33:767-777 (1985); Ishikawa, E., *Journal of Immunoassay.* 4:209-327 (1983); and in U.S. Pat. No. 4,190,496, for example, the entire contents of the above listed references being hereby incorporated by reference in their entireties.

The preferred enzymes and suitable substrates corresponding thereto include horseradish peroxidase for which suitable substrates are o-phenylenediamine, m-phenylenediamine, o-dianisidine, and 4-chloro-α-napthol. They also include β-galactosidase for which suitable substrates are 4-methylumbelliferyl-β-D-galactoside, p-nitrophenyl-β-D-galactose, p-nitrophenol, o-nitrophenyl-β-D-galactose, and onitrophenol, for example. They include alkaline phosphatase for which suitable substrates are p-nitrophenylphosphate, indoxyl phosphate, and 5-bromo-3-chloroindoxyl phosphate, for example.

Examples of suitable procedures for enzyme labeling the antibody include the use of carbodiimides, dialdehydes, and gluteraldehyde bifunctional coupling reagents. Linkage of enzymes through amine groups can be achieved by treating the proteins with thionyl chloride, N-hydroxysuccinimide or similar reagents in an anhydrous solvent such as dimethylformamide, dioxane, dimethylsulfoxide, tetrahydrofuran, or the like. Alternative coupling agents include carbodiimides such as 1-ethyl-3-(3-(N,N'-dimethylamino)propyl)-carbodiimide, 1-cyclohexyl-3-(2-morpholinoethyl)carbodiimide methyl-p-toluenesulfonate, succinimidyl 4-(N-maleimidoethyl)-cyclohexane-1-carboxylate, and succinimidyl 3-(2-pyridyldithio)-propionate, for example.

The carbohydrate moiety of an enzyme can also be oxidized to an aldehyde and reacted with lysyl amino groups of immunoglobulins to form a Schiff's base. Reduction with sodium borohydride effects a stable linkage of enzyme and antibody. Horseradish peroxidase with antibody can be efficiently linked to immunoglobulins by the method of Wilson, supra.

Fluorophore and chromophore labeled antibodies can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science.* 162:526 (1968) and Brand, L. et al, *Annual Review of Biochemistry.* 41:843-868 (1972). The antibodies can be labeled with fluorescent chromophore groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies can be labeled with fluorochromes or chromophores by the procedures described by Goding, J. (supra, pp 208-249).

The antibodies used in the methods of this invention can be covalently bonded to avidin or biotin in one embodiment of this invention. Suitable binding procedures involve cross-linking through a bifunctional cross-linking agent. Suitable bifunctional compounds are described by Peters, K. et al, *Ann.Rev.Biochim.* 46:523 (1977).

In other instances, the bonds can be formed directly between the reagents themselves. For example, antibody can be bound to avidin through functional groups on the respective materials. As a specific example, avidin can be treated with periodate and reacted with antibody to give a Schiff base formation without inhibiting the biotin to avidin binding or blocking immunological activity of the antibody.

Known techniques using bifunctional cross-linking agents include the following: (a) a one-step glutaraldehyde linkage, Avrameas, S., *Immunochemistry.* 6:43 (1969); (b) two-step glutaraldehyde linkage, Avrameas, S., *Immunochemistry.* 8:1175 (1971); and (c) dimaleimide linkage, Kato, K. et al, *Euro.J.Biochem.* 62:285 (1966).

Antibodies can be labeled with metallic radionuclides according the procedure of Hnatowich, D. et al. *Journal of Applied Radiation.* 35:554-557 (1984) and Buckley, R et al. *Federation of European Biochemical Societies.* 166:202-204 (Jan. 1984).

One embodiment of the immunoassay methods of this invention uses an insoluble support such as a polystyrene plate to which anti-(cellular fibronectin) antibody or anti-(fibronectin) antibody is adhered, either directly or through a goat anti-mouse antibody. It is contacted with a sample diluted with an aqueous buffer solution such as phosphate buffer solution (PBS), pH 6 to 8 and preferably from 7.2 to 7.6 for a sufficient time to permit binding of cellular fibronectin in the sample with the antibody on the insoluble support, and then removing the sample from the support. The incubation time should be sufficient to permit substantial binding to occur, the time being temperature dependent. Suitable incubation times are from 30 to 240 minutes at temperatures within the range of from 16° to 40° C., the preferred contact time being at least 60 minutes at temperatures within the range of from 20° to 26° C. The residual sample solution is then removed from the support by use of a rinse solution. Any conventional rinse solution can be used. A suitable rinse solution is described in U.S. Pat. No. 4,528,267. It is an aqueous phosphate buffer solution having a phosphate molarity of from 0.0001 to 0.05, a pH of from 6 to 8 and containing from 0.001 to 0.1 weight percent of non-ionic surfactant. Suitable non-ionic surfactants include polyoxyethylene ethers (BRIJ such as lauryl, cetyl, oleyl, stearyl, and tridecyl polyoxyethylene ethers); polyoxyethylene sorbitans (TWEEN such as polyoxyethylene sorbital monolaurate, monopalmitate, monostearate, monoleate, and trioleates); and other polyoxyethylene ethers (TRITON, for example).

The insoluble support is then contacted with a secondary antibody which will bind with the captured cellular fibronectin on the insoluble support, the sandwiching antibody. The sandwiching antibody can be labeled or unlabeled. In the event that an unlabeled sandwiching antibody is used, a tertiary antibody which binds with the sandwiching antibody and which bears a physically detectable label can be used in a conventional manner to determine the sandwiching antibody.

A variety of labels have been described above. For purposes of clarity and not by way of limitation, the subsequent steps of the process will be described for anti-(cellular fibronectin) antibodies which have been labeled with an enzyme, preferably a chromogenic or a fluorogenic enzyme. The term "chromogenic enzyme" is defined herein to refer to an enzyme which will produce a chromophore product with a suitable substrate. The term "fluorogenic enzyme" is defined herein to refer to an enzyme which will produce a fluorophore product with a suitable substrate.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit the sandwiching antibody to bind with exposed cellular fibronectin epitopes, if any, adhering to the insoluble support.

The sandwiching antibody solution is then removed from the insoluble support, and the support is rinsed with a rinse solution such as described above, to remove any residual, unbound labeled material.

If the sandwiching antibody is unlabeled, an enzyme labeled antibody or other binding agent which binds selectively with the sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit labeled anti-(cellular fibronectin) antibody to bind with exposed cellular fibronectin antigen epitopes, if any, adhering to the insoluble support.

The labeled antibody solution is then removed from the insoluble support, and the support is rinsed with a rinse solution such as described above, to remove any residual, unbound labeled material.

In a next step of the sandwich process of this invention, the insoluble support is contacted with an aqueous solution of a substrate which undergoes a reaction in the presence of the enzyme to release fluorescent or chromogen compound into the solution. Suitable substrates and the enzymes which they can be converted are described in U.S. Pat. Nos. 4,190,496 and 4,528,267, for example. The support is contacted with an aqueous solution of the substrate containing from $10^{-2}$ to $10^{-10}$ molar concentrations of the substrate. Substrate molar concentrations of from $10^{-4}$ to $10^{-5}$ are preferred. Preferred additional reagents and buffers in the substrate solution include 2-amino-2-methyl-1-propanol buffer, TRIS, and magnesium chloride, for example.

The substrate solution is incubated with the insoluble support for sufficient time for the reaction yielding the fluorophore or chromophore to occur. At temperatures of from 18° to 40° C., incubation times of from 5 to 240 minutes can be used. Preferably, the temperature is within the range of from 20° to 26° C., and the incubation time is from 30 to 120 minutes.

The fluorescent or chromophore level in the solution is then measured. The equipment and procedures for determining the level of fluorescence or chromophore level in the substrate solutions are those conventionally used in the art. The level of fluorescence or chromogen in solution is a function of the enzyme concentration on the insoluble support which is, in turn, a function of the amount of cellular fibronectin in the sample. The concentration of the cellular fibronectin can be determined by comparing the fluorescence or chromophore level of the solution with respective fluorescence or chromophore levels obtained with control solutions containing known concentrations of cellular fibronectin.

In a membrane embodiment of the immunoassay methods of this invention, an insoluble support to which anti-(fibronectin) antibody is adhered is contacted with blood, serum or plasma sample diluted with an aqueous buffer solution such as phosphate buffer solution (PBS), pH 6 to 8 and preferably from 7.2 to 7.6 for a sufficient time to permit binding of cellular fibronectin in the sample with the anti-(fibronectin) antibody on the insoluble support. The time required for binding is very small in a flow through system. Suitable incubation times can be one sec up to 20 min at temperatures within the range of from 16° to 40° C., the preferred contact time being less than one min and optimally from 10 sec to 2 min.

The insoluble support is then contacted with an anti-(cellular fibronectin) antibody, the sandwiching antibody. The sandwiching antibody can be labeled or unlabeled. In the event that an unlabeled sandwiching antibody is used, a secondary antibody which binds with the sandwiching antibody and which bears a physically detectable label can be used in a conventional manner to determine the sandwiching antibody.

A variety of labels have been described above. For purposes of clarity and not by way of limitation, the subsequent steps of the process will be described for anti-(cellular fibronectin) antibodies which have been labeled with an enzyme, preferably a chromogenic enzyme.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit the sandwiching antibody to bind with exposed cellular fibronectin epitopes, if any, adhering to the insoluble support.

The sandwiching antibody solution optionally can be removed from the insoluble support, and the support is rinsed with a rinse solution such as described above, to remove any residual, unbound labeled material.

If the sandwiching antibody is unlabeled, an enzyme labeled antibody or other binding agent which binds selectively with the sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit labeled anti-(cellular fibronectin) antibody to bind with exposed cellular fibronectin epitopes, if any, adhering to the insoluble support. The preferred incubation times and temperatures are as set forth for the binding of insolubilized reagent anti-(cellular fibronectin) antibody with the endocellular fibronectin antigen (or complex thereof).

The labeled antibody solution is then removed from the insoluble support, and the support is rinsed with a rinse solution such as described above, to remove any residual, unbound labeled material.

In a next step of the sandwich process of this invention, the insoluble support is contacted with an aqueous solution of a substrate which undergoes a reaction in the presence of the enzyme to release chromogen compound into the solution. Suitable substrates and the enzymes which they can be converted are described in U.S. Pat. Nos. 4,190,496 and 4,528,267, for example. The support is contacted with an aqueous solution of the substrate containing from $10^{-2}$ to $10^{-10}$ molar concentrations of the substrate. Preferred additional reagents and buffers in the substrate solution include 2-amino-2-methyl-1-propanol buffer, TRIS, and magnesium chloride, for example.

The substrate solution is incubated with the insoluble support for sufficient time for the reaction yielding the fluorophore or chromophore to occur. At temperatures of from 18° to 40° C., incubation times of from 1 to 20 min can be used. Preferably, the temperature is within the range of from 20° to 26° C., and the incubation time is from 2 to 5 min. The chromogen level on the membrane can be measured using a reflectometer or densitometer.

The kits of this invention comprise combinations of buffers for transport and storage with sampling devices such as sampling devices; supports having reagents of this invention adhered thereto; vials, foil packages or other containers of reagents of this invention; and combinations thereof. Each of the insoluble support structures in a foil package can be combined with other reagents in vials or other packages. They can also be combined with other, optional reagents such as stop reagents in separate vials or other packages.

Reagents of this invention include anti-(endothelial cell marker) antibody adhered to an insoluble reagent support, preferably wherein the anti-(endothelial cell marker) antibody is an anti-(cellular fibronectin) antibody; and an endothelial cell marker adhered to an insoluble reagent support, preferably when the endothelial cell marker is a cellular fibronectin.

One testing kit of this invention includes an anti-(endothelial cell marker) antibody adhered to an insoluble support and labeled anti-(endothelial cell marker) antibody. The anti-(endothelial cell marker) antibody adhered to the insoluble support and the labeled anti-(endothelial cell marker) antibody can be anti-(cellular fibronectin) antibodies, preferably which do not significantly cross-react.

Another testing kit comprises an anti-(cellular fibronectin) antibody adhered to an insoluble support and labeled anti-(fibronectin) antibody. Still another comprises an anti-(fibronectin) antibody adhered to an insoluble support and labeled anti-(cellular fibronectin) antibody. A still other testing kit comprises an anti-(endothelial cell marker) antibody adhered to an insoluble support and labeled endothelial cell marker wherein the anti-(endothelial cell marker) antibody can be an anti-(cellular fibronectin) antibody and the labeled endothelial cell marker can be labeled cellular fibronectin. A still further testing kit comprises an endothelial cell marker adhered to an insoluble support and labeled anti-(endothelial cell marker) antibody wherein the endothelial cell marker can be a cellular fibronectin and the labeled anti-(endothelial cell marker) antibody can be labeled anti-(cellular fibronectin) antibody.

This invention is further illustrated by the following specific, but non-limiting examples. Temperatures are given in degrees Centigrade and percents as weight percents unless otherwise specified. Examples which are constructively reduced to practice herein are presented in the present tense, and examples representing laboratory experiments previously reduced to practice are presented in the past tense.

EXAMPLE 1

Polyclonal Anti-(cellular fibronectin) Antibodies

Cellular fibronectin is purified from human endothelial cells as described by Engvall and Ruoslahti, *Int.J.-Cancer.* 20:1–5 (1977).

The anti-(cellular fibronectin) antibodies are elicited in rabbits using the immunization techniques and schedules described in the literature, e.g., Stollar, *Methods of Enzymology.* 70:70 (1980), immunizing the rabbits with the cellular fibronectin antigen. The antiserum is screened in a solid phase assay similar to that used for monoclonal antibodies, e.g., as described by Lange et al, *Clin.Exp.Immunol.* 25:191 (1976) and Pisetsky et al, *J.Immun.Methods.* 41:187 (1981).

The IgG fraction of the antisera is purified further by affinity chromatography using CNBr-Sepharose 4B (Pharmacia Fine Chemicals) to which has been coupled cellular fibronectin. The method used for coupling is that recommended by the gel manufacturer, AFFINITY CHROMATOGRAPHY. Pharmacia Fine Chemicals, pp 15–18.

The column is equilibrated with from 2 to 3 volumes of buffer (0.01M PBS, pH 7.2), and the anti-(cellular fibronectin) antibody containing solution is then applied to the column. The absorbency of the eluate is monitored at 280 nm until protein no longer passes from the column. The column is then washed with 0.1M glycine buffer, pH 2.5, to desorb the immunoaffinity bound anti-(cellular fibronectin) antibody. Peak protein fractions are collected, pooled and dialyzed against 0.01M PBS, pH 7.2, for 24–36 hr at 4° C. with multiple buffer changes.

If a higher purity is desired, the affinity purified IgG can be passed through an plasma fibronectin bound affinity column by the procedure described above to remove any antibodies which would cross-react with plasma fibronectins.

EXAMPLE 2

Monoclonal Anti-(endothelial cell fibronectin/ Antibody

Using the purified endothelial cell fibronectin obtained by the procedure of Example 1, mouse monoclonal antibodies to the cellular fibronectin are obtained using standard procedures of Galfre and Milstein, *Methods in Enzym.* 73:1 (1981) and Matsurra, H. and Hakomori, S. et al (supra), using cellular fibronectin as the antigen for immunizing the mice. The monoclonal antibodies are screened using a modification of the techniques described in the literature, e.g., Lange et al, *Clin.Exp.Immunol.* 25:191 (1976) and Pisetsky et al, *J.Immun.Methods.* 41:187 (1981).

Mouse monoclonal antibody is purified from ascites fluid or from hybridoma culture supernatants using Protein-A coupled Sepharose-4B (Pharmacia Fine Chemicals) according to the procedure of Tijsson, PRACTICE AND THEORY OF ENZYME IMMUNOASSAYS. Elsevier Science Publishers, pp 105–107 (1985).

EXAMPLE 3

Polyclonal Antibody Coated Microtiter Plate

Rabbit anti-(cellular fibronectin) antibodies prepared and further purified to remove plasma fibronectin cross-reactivity as described in Example 1 is diluted to 10 μg/mL in 0.05M carbonate buffer, pH 9.6. 100 μL is dispersed into each well of an IMMULON II microtiter plate (Dynatech). The plate is covered and incubated 4 hr at room temperature or 4° C. overnight. The plate is washed 4 times with Wash Buffer (0.02M Tris HCl, 0.015M NaCl, 0.05% TWEEN-20), filling and emptying the wells completely with each use. The plate is then blocked by dispensing into each well 200 μL of a blocking solution (0.01M PBS, 1% BSA, 0.02% NaN$_3$, pH 7.4) and incubating for 1 hr at room temperature. The wells are then washed 4 times with Wash Buffer, as described above. The plate is now ready for immunoassay of samples.

EXAMPLE 4

Monoclonal Antibody Coated Micotiter Plate

Goat F(ab')$_2$ anti-mouse IgG antibody (Tago) is diluted to 10 μg/mL in 0.05M carbonate buffer, pH 9.6. 100 μL is dispensed into each well of an IMMULON II microtiter plate(Dynatech). The plate is covered and incubated 4 hr at room temperature or 4° C. overnight. The plate is washed 4 times with Wash Buffer as described in Example 3. The plate is then blocked by dispensing into each well the Blocking Solution as described in Example 3. Mouse monoclonal anti-cellular fibronectin ascites prepared as in Example 2 is diluted 1/500 with 0.01M PBS-1% BSA, pH 7.4. 100 μL of the solution is dispensed into each well of the blocked microtiter plate. The wells are incubated, covered, for 2 hr at room temperature or overnight at 4° C. The plate is then washed 4 times with Wash Buffer as described above, and is then ready for immunoassay of samples.

EXAMPLE 5

Enzyme Labeled Anti-(cellular fibronectin) Antibody

Anti-(cellular fibronectin) antibody prepared in accordance with the procedures of Example 1 or Example 2 is conjugated with alkaline phosphatase following the one-step glutaraldehyde procedure Avrameas, *Immunochemistry.* 6:43 (1969).

EXAMPLE 6

Sandwich Immunoassay

Positive and negative controls are included in the test. The positive control is purified human cellular fibronectin of known concentration, appropriately diluted to fall within the assay range (20 ng/mL to 5 μg/mL for a monoclonal based assay). The negative control is sample diluent. The Assay Standard is purified human cellular fibronectin of known fibronectin concentration, serially diluted in sample diluent to provide a standard curve, ranging from 20 ng to 10 μg/mL.

The sample diluent is the anti-protease cocktail described in copending application Ser. No. 244,984 filed Sept. 15, 1988, the entire contents of which are hereby incorporated by reference. It protects fibronectin-containing samples from proteolytic degradation during transit and storage. The solution consisted of 0.05M Tris-HCl, pH 7.4; 0.15M NaCl, 0.02% NaN$_3$, 1% BSA, 500 Kallikrein Units/mL of aprotinin, 1nM phenylmethylsulfonyl fluoride (PMSF) and 5 mM EDTA.

Blood samples are obtained from the patient and processed to yield a plasma or serum sample.

A microtiter plate prepared as in Example 3 or 4 is used for the assay. 100 μL of each standard, sample, positive and negative control are placed in separate wells and incubated 2 hr at room temperature. The plate is washed 4 times with Wash Buffer as described in Examples 3 and 4. 100 μL of alkaline phosphatase-conjugated goat anti-(cellular fibronectin) prepared as in Example 5 is diluted 1/1000 in Conjugate Buffer (0.02M Tris-HCl, pH 8, 0.3M NaCl, 0.05% TWEEN 20, 5% BSA, 0.02% NaN$_3$). 100 μL is dispensed into each well and incubated for 2 hr at room temperature. The plate is washed 4 times as previously described. 4 mg/mL of p-nitrophenylphosphate (PNPP) is used as the substrate. This is diluted in 0.18M 2-amino-2-methyl-1-propanol (AMP) buffer, pH 9.5 with 0.12 mM MgCl$_2$. 100 μL is dispensed into each well of the microtiter plate. After a 5 min incubation at room temperature, the reaction rate in milli-OD/min is read at 405 nm on a V-MAX ™ kinetic microtiter plate reader (Molecular Devices).

A standard curve was constructed by correlating increasing reaction rate with increasing cellular fibronectin concentration in the standards. Unknowns were calculated directly from the curve or by using a pre-set computer program (Molecular Devices).

We claim:

1. A method for determining preeclampsia, pregnancy induced hypertension or eclampsia comprising
   a) contacting a blood, plasma or serum sample from a pregnant patient with an anti-(cellular fibronectin) antibody;
   b) determining binding by said antibody to determine the presence of cellular fibronectin in the sample; and
   c) comparing the presence of cellular fibronectin to a standard wherein an increase of said fibronectin is indicative of the presence of one of the above set forth physiological conditions.

2. The method of claim 1 comprising the steps of
   a) contacting the sample with an insoluble support to which anti-(cellular fibronectin) antibody is adhered for a time sufficient to permit antigen-antibody binding to occur;
   b) contacting the insoluble support with an anti-(fibronectin) antibody for a time sufficient to permit antigen-antibody binding to occur; and
   c) determining the presence of anti-(fibronectin) antibody on the insoluble support.

3. The method of claim 2 wherein the anti-(fibronectin) antibody has a physically detectable label.

4. The method of claim 2 wherein the anti-(fibronectin) antibody is an anti-(cellular fibronectin) antibody.

5. The method of claim 4 wherein the anti-(cellular fibronectin) antibody adhered to the insoluble support is a first anti-(cellular fibronectin) antibody, and the anti-(fibronectin) antibody is a second anti-(cellular fibronectin) antibody which does not significantly cross-react with the first anti-(cellular fibronectin) antibody.

6. The method of claim 1 comprising the steps of
   a) contacting a mixture of the sample and an anti-(fibronectin) antibody with an insoluble support to which an anti-(cellular fibronectin) antibody is adhered for a time sufficient to permit antigen-antibody binding to occur; and
   b) determining the presence of anti-(fibronectin) antibody on the insoluble support.

7. The method of claim 6 wherein the anti-(fibronectin) antibody has a physically detectable label.

8. The method of claim 6 wherein the anti-(cellular fibronectin) antibody is a first anti-(cellular fibronectin) antibody and the anti-(fibronectin) antibody is a second anti-(cellular fibronectin) antibody which does not significantly cross-react.

9. The method of claim 1 comprising the steps of
   a) contacting the sample with an insoluble support to which anti-(fibronectin) antibody is adhered for a time sufficient to permit antigen-antibody binding to occur;
   b) contacting the insoluble support with an anti-(cellular fibronectin) antibody for a time sufficient to permit antigen-antibody binding to occur; and
   c) determining the presence of anti-(cellular fibronectin) antibody on the insoluble support.

10. The method of claim 9 wherein the anti-(cellular fibronectin) antibody has a physically detectable label.

11. The method of claim 1 comprising the steps of
    a) contacting a mixture of the sample and an anti-(cellular fibronectin) antibody with an insoluble support to which an anti-(fibronectin) antibody is adhered for a time sufficient to permit antigen-antibody binding to occur; and
    b) determining the presence of anti-(cellular fibronectin) antibody on the insoluble support.

12. The method of claim 11 wherein the anti-(cellular fibronectin) antibody has a physically detectable label.

13. The method of claim 1 comprising
    a) contacting an insoluble support to which an anti-(cellular fibronectin) antibody is adhered with a mixture of the sample and an amount of a labeled cellular fibronectin which is insufficient to bind with all of the anti-(cellular fibronectin) antibody adhered to the support; and
    b) determining the amount of labeled cellular fibronectin bound to the insoluble support or the amount of labeled cellular fibronectin remaining in the mixture.

14. The method of claim 1 comprising
    a) contacting an insoluble support to which cellular fibronectin is adhered with a mixture of the sample and an amount of a labeled anti-(cellular fibronectin) antibody which is insufficient to bind with all of the cellular fibronectin adhered to the support; and
    b) determining the amount of labeled anti-(cellular fibronectin) antibody bound to the insoluble support or the amount of labeled anti-(cellular fibronectin) antibody remaining in the mixture.

* * * * *